United States Patent [19]

Clark et al.

[11] 4,000,286

[45] Dec. 28, 1976

[54] 3-PHENYL,3H 1,2,3 TRIAZOLO[4,5-B]PYRIDINES

[75] Inventors: Robert L. Clark, Woodbridge; Arsenio A. Pessolano, Colonia; Tsung-Ying Shen, Westfield, all of N.J.

[73] Assignee: Merck & Co., Inc., Rahway, N.J.

[22] Filed: Oct. 3, 1975

[21] Appl. No.: 619,531

Related U.S. Application Data

[63] Continuation-in-part of Ser. No. 601,671, May 28, 1975, abandoned.

[52] U.S. Cl. .................... 424/263; 260/294.9; 260/295 AM; 260/295 K; 260/296 R; 260/296 B; 260/296 D; 260/296 H
[51] Int. Cl.² ............... C07D 471/04; A61K 31/44
[58] Field of Search ............... 260/296 H; 424/263

[56] References Cited

FOREIGN PATENTS OR APPLICATIONS 1,268,772   3/1972   United Kingdom

OTHER PUBLICATIONS

Vohra et al. "J. Med. Chem." vol. 8 (1965) pp. 296–304.
Ahmad et al. "Chem. Abstracts" vol. 68 (1968) No. 94537j.
Ahmad "Chem. Abstracts" vol. 70 (1969) No. 45865x.

*Primary Examiner*—Henry R. Jiles
*Assistant Examiner*—R. W. Ramsuer
*Attorney, Agent, or Firm*—Frank M. Mahon; Harry E. Westlake, Jr.; Stanley E. Anderson, Jr.

[57] ABSTRACT

3H-1,2,3-Triazolo[4,5-b]pyridines substituted in the 3-position have utility as analgesic, anti-inflammatory and anti-pyretic agents. They are prepared by diazotization of a 3-amino-2-(substitute) aminopyridine.

5 Claims, No Drawings

3-PHENYL,3H 1,2,3 TRIAZOLO[4,5-b]PYRIDINES

This application is a continuation-in-part of our application Ser. No. 601,671, filed May 28, 1975 now abandoned.

This invention is concerned with novel 3H-1,2,3-triazolo[4,5-b]pyridines, processes for their preparation, pharmaceutical compositions comprising the novel compounds as active ingredient, and the method of treating pain, inflammation, and fever with the novel compounds and compositions.

In particular, it is concerned with compounds of structural formula:

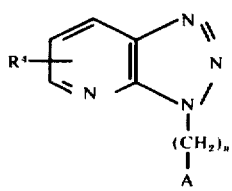

wherein
n is 0–3 and
A is
1. pyridyl, either unsubstituted or substituted with lower alkyl, especially $C_{1-3}$alkyl,
2. lower cycloalkyl, especially $C_{3-6}$cycloalkyl,
3.

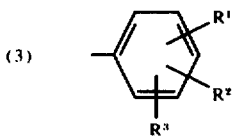

wherein $R^1$ and $R^2$ are the same or different and each is
 a. hydrogen,
 b. lower alkoxy, especially $C_{1-3}$alkoxy, either straight or branched chain,
 c. lower alkyl, especially $C_{1-5}$ alkyl,
 d. halo, such as chloro, bromo, or fluoro,
 e. trifluoromethyl,
 f. amino, either unsubstituted or substituted with lower alkyl, especially $C_{1-5}$ alkyl,
 g. phenoxy,
 h. cyano,
 i. carbamoyl,
 j. hydroxy,
 k. lower alkanoyl, preferably $C_{2-3}$ alkanoyl,
or $R^1$ and $R^2$ on adjacent carbon atoms taken together represent
 a. —O—(CH$_2$)$_m$—O— wherein m is 1–3,
 b. —CH$_2$—O—CH$_2$,
 c. —(CH$_2$)$_3$—,
$R^3$ is a. hydrogen,
 b. lower alkoxy, especially $C_{1-3}$ alkoxy, or
 c. lower alkyl, especially $C_{1-5}$ alkyl,
$R^4$ is
 1. hydrogen or
 2. lower alkyl, especially $C_{1-5}$ alkyl.

An important embodiment of the present invention is the novel compounds wherein n is 0.

Another important embodiment of this invention is the novel compounds wherein n is 0, and A is

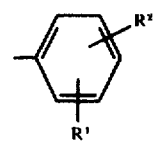

wherein $R^1$ and $R^2$ are the same or different and are hydrogen or fluoro.

Another important embodiment of this invention is the novel compounds wherein n is zero and A is pyridyl or $C_{1-3}$ alkylpyridyl.

The compounds of this invention are prepared in accordance with the following procedure:

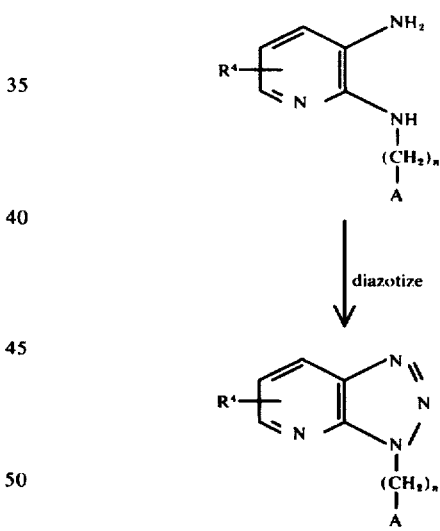

The process comprises slow addition of at least a molar equivalent of sodium nitrite in water solution to a cold (0°–10° C.), stirred solution of the diamino-pyridine mineral acid addition salt in water or mineral acid solution, optionally containing a little lower alkanol such as ethanol, and continuing the stirring for 10–60 minutes after addition is complete. The product is recovered by filtration either before or after neutralization and, if necessary, recrystallized.

The key intermediate in the above-described process is the diaminopyridine, and it is prepared by the following process:

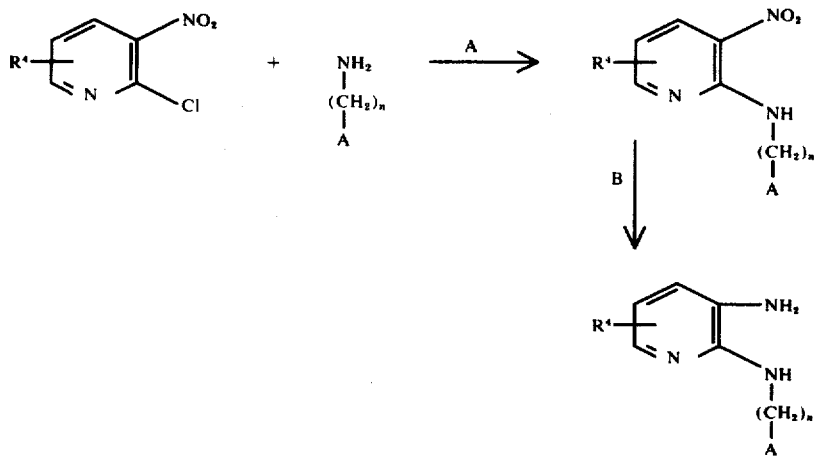

Step A of the above reaction scheme proceeds very readily, simply by forming a mixture of the chlornitropyridine and 2-3 equivalents of the amino compound, warming if necessary until an exothermic reaction ensues, usually at about 80 to about 170° C., and if necessary, controlling the temperature below about 250° C. for 10–60 minutes.

Because of the exothermic nature of the reaction, it is often found convenient to conduct it in refluxing acetic acid in the presence of an equimolar amount of sodium acetate until the condensation is complete, usually requiring 2 to about 10 hours.

The condensation may also be performed in a refluxing high boiling solvent such as dimethylformamide optionally in the presence of an acid acceptor such as an alkali metalcarbonate and copper powder to catalyze the reaction.

The more basic the amino compound the more easily the reaction proceeds. With the alkylamines, i.e. where $n = 1-3$, the reaction begins spontaneously at room temperature.

Step B in the synthesis of the key intermediate comprises catalytic reduction of the nitro group with hydrogen in the presence of an hydrogenation catalyst, such as platinum or palladium or Raney nickel, in a lower alkanol or lower alkanolic acetic acid solution. The resulting diaminopyridine is usually susceptible to air oxidation, turning black very quickly. In practice, it is therefore advisable to add an excess of a mineral acid, especially hydrochloric acid or gaseous hydrogen chloride, to the filtrate after separation of the catalyst. Because of this instability, the key intermediate, diaminopyridine acid addition salt, is frequently not isolated, but rather held in acid solution and used as such in the final process for conversion to the triazolopyridines of this invention, The novel compounds of this invention are potent analgesic agents as measured by the modified Randall Selitto test (Winter el al., *J. Pharmacol. Exptl. Ther.*, 150, 165-171 (1965)) which is known to correlate well with activity in mammals. They are also anti-inflammatory and anti-pyretic agents.

It is therefore an object of the present invention to provide a method of treating pain and/or inflammation with the novel compounds of this invention by the administration of active compound at the rate of 0.5 to 50 mg./kg./day, preferably from 4–15 mg./kg./day in a suitable pharmaceutical formulation, which is another embodiment of this invention, adapted for oral, topical, parenteral, inhalation, or rectal administration.

The pharmaceutical formulations for oral use may be in the form of tablets, troches, lozenges, aqueous or oral suspensions, dispersible powders or granules, emulsions, hard or soft capsules, syrups or elixirs, and may be prepared according to methods known in the art for the manufacture of such compositions.

The pharmaceutical formulations for rectal use are in the form of suppositories prepared according to art recognized methods.

For topical use, creams, ointments, gels, solutions, or suspensions are employed.

The amount of active ingredient combined with the carrier materials of the pharmaceutical formulations to produce a single dosage form will vary depending on the mode of administration. For example, oral preparations should comprise from 5–500 mg. and preferably about 50–250 mg. of active compound in combination with the carrier materials.

EXAMPLE 1

3-(2,4-Difluorophenyl)-3H-1,2,3,-Triazolo[4,5-b]pyridine

Step A: Preparation of
2-(2,4-difluoroanilino)-3-nitropyridine

A mixture of (7.9 g., 0.05 mole) 2-chloro-3-nitropyridine and 12.9 g. (0.10 mole) of 2,4-difluoroaniline was purged with nitrogen and heated in an oil bath to 110° C. when the temperature rose spontaneously to 135° C. Heating was continued to 145° C. when a second spontaneous temperature rise occurred requiring temperature control with ice. The maximum internal temperature was 185° C. After slight cooling, 40 ml. of acetic acid and 60 ml. of water was added. After stirring one hour the crystalline precipitate was collected (11.1 g., m.p. 110° C.) and recrystallized from hexane to give 2-(2,4-difluoroanilino)-3-nitropyridine, m.p. 112°–114° C.

Step B: Preparation of
3-amino-2-(2,4-difluoroanilino)pyridine

The nitro compound (11 g.) from Step A was hydrogenated in 150 ml. of methanol and 10 ml. of acetic acid with one-half teaspoon of Raney nickel for 2 hours. The catalyst was removed on a filter and the filtrate was evaporated in vacuo. The residue was dissolved in 75 ml. of 2.5 N hydrochloric acid and 75 ml. of water and the solution was treated with decolorizing charcoal twice. The final filtrate was kept and used directly in the next step.

Step C: Preparation of 3-(2,4-difluorophenyl)-3H-1,2,3-triazolo[4,5-b]pyridine One-half of the above acid solution was cooled and stirred in ice as a solution of 1.5 g. (0.022 mole) of sodium nitrite in 30 ml. of water was added over 25 minutes keeping the temperature below 5° C. After an additional 15 minutes in the ice-bath, the precipitate was collected (2.6 g., m.p. 132° C.) and recrystallized from 50 ml. of benzene by adding to the warm solution 75 ml. of petroleum ether to give 1.6 g. of 3-(2,4-difluorophenyl)-3H-1,2,3-triazolo[4,5-b]pyridine, m.p. 138–139.

Employing the procedure substantially as described in Example 1, but substituting for the 2,4-difluoroaniline used in Step A thereof, an equimolar amount of an amine of structure:

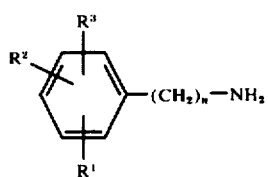

followed by reduction substantially as described in Step B, followed by diazotization with sodium nitrite substantially as described in Step C, there are produced respectively the nitroaminopyridines, diaminopyridines, and 3H-1,2,3-triazolo[4,5-b]pyridines described in Table I in accordance with Equation I:

Equation I

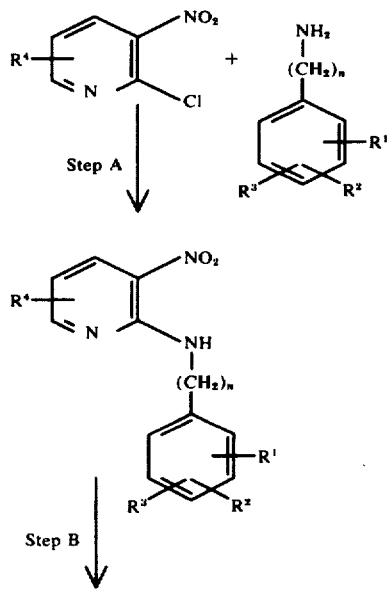

-continued
Equation I

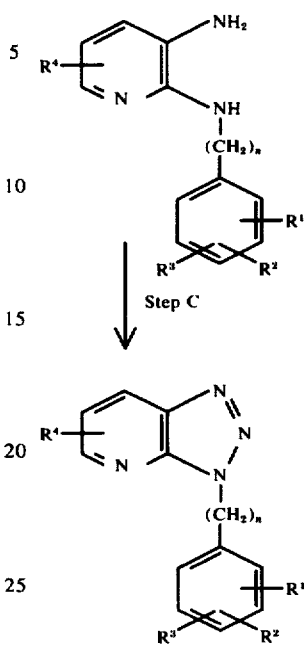

Table I

| $R^1$ | $R^2$ | $R^3$ | $R^4$ | n | m.p. (° C) nitro-anilino-pyridine | m.p. (° C) triazolo-[4,5-b]-pyridine |
|---|---|---|---|---|---|---|
| 4-OCH$_3$ | H | H | H | 0 | 78–80 | 129–130 |
| 2-F | 5-CH$_3$ | H | H | 0 | 114–117 | 107–108 |
| 4-F | H | H | H | 0 | 130–131 | 182–184 |
| 3-CF$_3$ | H | H | H | 0 | 81–82 | 100 |
| 3-F | H | H | H | 0 | 102–104 | 144–145 |
| 2-Br | H | H | H | 0 | 138–140 | 116–118 |
| 2-CH$_3$ | 4-CH$_3$ | H | H | 0 | 121–125 | 124–125 |
| 2-CH$_3$ | 3-Cl | H | H | 0 | 134–135 | 152–153 |
| 4-Cl | H | H | H | 0 | 146–147 | 162–163 |
| 3-O—CH$_2$—O-4* | | H | H | 1 | 113–115 | 107–108 |
| 2-F | H | H | H | 0 | 102–103 | 117–118 |
| H | H | H | H | 0 | 71–73 | 76–77 |
| 3-CN | H | H | H | 0 | 155–157 | 165–166 |

*Step A reaction begins spontaneously at room temperature.

EXAMPLE 2

3-(2,5-difluorophenyl)-3H-1,2,3-Triazolo[4,5-b]pyridine

Step A: Preparation of 2-(2,5-difluoroanilino)-3-nitropyridine

A mixture of 5 g. (0.0315 mole) of 2-chloro-3-nitropyridine and 12.9 g. (0.1 mole) of 2,5-difluoroaniline was heated in an oil bath and under nitrogen to 120° C. when the temperature rose spontaneously to 160° C. It was heated further to 180° C. and held there for 10 minutes. After cooling slightly there was added 50 ml. of a 50% aqueous acetic acid solution. The precipitate was collected, dissolved in 75 ml. of hot benzene, filtered, concentrated to about 25 ml. and crystallized by addition of petroleum ether to give 6.8 g. of 2-(2,5-difluoroanilino)-3-nitropyridine, m.p. 150°–152° C.

Step B: Preparation of 3-amino-2-(2,5-difluoroanilino)-pyridine hydrochloride The nitro compound (6.5 g.) from Step A was hydrogenated in 150 ml. of methanol over 0.35 g. of 5% platinum on carbon for 25 minutes. The catalyst was removed by filtration and the filtrate was evaporated in vacuo. The residue was dissolved in 75 ml. of 2.5 N hydrochloric acid and 50 ml. of water. After standing at room temperature, the product crystallized to give 5.5 of 3-amino-2-(2,5-difluoroanilino)pyridine hydrochloride,

Step C: Preparation of 3-(2,5-difluorophenyl)-3H-1,2,3,-triazolo[4,5-b]pyridine The product from Step B (3.0 g.) was suspended in 50 ml. of warm ethanol and 25 ml. of 2.5 N hydrochloric acid. To the stirred ice-cooled mixture was added a solution of 1 g. of sodium nitrite in 25 ml. of water over 20 minutes and below 5° C. After another 15 minutes at ice temperature, the precipitate was collected (2.5 g. m.p. 140° C.) and recrystallized from 40 ml. of benzene and petroleum ether to give 2.1 g. of 3-(2,5-difluorophenyl)-3H-1,2,3-triazolo[4,5-b]pyridine, m.p. 144°–145° C.

Employing the procedure substantially as described in Example 2, but substituting for the 2,5-difluoroaniline and the 2-chloro-3-nitropyridine used in Step A thereof, an equimolar amount of an amine of structure:

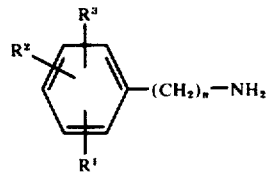

and a pyridine of structure

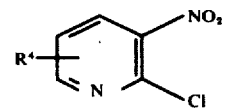

respectively, followed by reduction substantially as described in Step B, optionally with an equal weight of 5% palladium on carbon in place of the platinum on carbon, followed by diazotization with sodium nitrite substantially as described in Step C, there are produced respectively the nitroaminopyridines, diaminopyridines, and 3H-1,2,3-triazolo[4,5-b]pyridines described in Table II in accordance with Equation I.

Table II

| Catalyst | $R^1$ | $R^2$ | $R^3$ | $R^4$ | n | m.p. (° C.) nitro-anilino-pyridine | m.p. (° C.) triazolo-[4,5-b]-pyridine |
| --- | --- | --- | --- | --- | --- | --- | --- |
| Pd/C | 2-Cl | 4-Cl | H | H | 0 | 144–145 | 150–151 |
| Pd/C | 2-F | 6-F | H | H | 0 | — | 173–174 |
| Pd/C | 4-Et | H | H | H | 0 | 83–84 | 61–62 |
| Pd/C | 4-NH$_2$+++ | H | H | H | 0 | 176–177++++ | 186–187 |
| Pd/C | 2-Cl | H | H | H | 0 | 128–129 | 100–101 |
| Pd/C | 2-CH$_3$ | 6-CH$_3$ | H | H | 0 | 114–115 | 155–156 |
| Pd/C | 2-CH(CH$_3$)$_2$ | H | H | H | 0 | 96–98 | oil |
| Pd/C | H+ | H | H | H | 2 | 86–87 | 69–70 |
| Pt/C | 2-F++ | H | H | H | 1 | 116–118 | 84–85 |
| Pd/C | 4-O—C$_6$H$_5$ | H | H | H | 0 | 105–107 | 60–61 |
| Pd/C | 3-OCH$_3$ | H | H | H | 0 | 98–100 | 78–80 |
| Pt/C | 3-Cl | 4-Cl | H | H | 0 | 167–168 | 175–176 |
| Pd/C | 2-N(CH$_3$)$_2$ | H | H | H | 0 | — | 78–79 |
| Pd/C | 4-COCH$_3$ | H | H | H | 0 | 155–157 | 184–185 |
| Pd/C | 2-F | H | H | 6-CH$_3$ | 0 | 111–113 | 122–123 |

+Step A reaction begins spontaneously at room temperature.
++Step A reaction begins spontaneously at room temperature and is conducted in benzene solution.

+++The starting material was H$_2$N—⟨C$_6$H$_4$⟩—NHCOCH$_3$.

The —COCH$_3$ group was hydrolyzed either during reduction of the nitro compound or the ring closure.

++++The structure of this product is

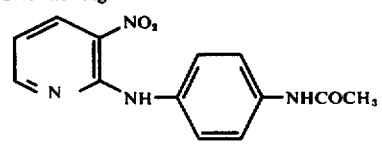

EXAMPLE 3

3-(2-Methoxyphenyl)-3H-1,2,3-triazolo[4,5-b]pyridine

Step A: Preparation of 2-(2-methoxyanilino)-3-nitropyridine

A mixture of 15.9 g. (0.10 mole) of 2-chloro-3-nitropyridine, 12.3 g. (0.10 mole) of 2-methoxyaniline, 8.2 g. (0.10 mole) of sodium acetate in 300 ml. of acetic acid was refluxed 1 hour. The mixture was concentrated in vacuo, and the residue was diluted with water. The precipitate was collected (18.1 g.). The solids were boiled with 80 ml. of ethanol and cooled to room temperature. The product was collected to give 13.7 g. of 2-(2-methoxyanilino)-3-nitropyridine, m.p. 151°–153° C.

Step B: Preparation of 2-(2-methoxyanilino)-3-aminopyridine hydrochloride

The nitro compound (13.7 g.) from Step A was hydrogenated in 300 ml. of ethanol over ¼ teaspoon of Raney nickel with hydrogen for 18 hours. The catalyst was removed on a filter and hydrogen chloride gas was bubbled into the filtrate for several minutes. Ether was added to complete crystallization of 10.5 g. of 2-(2-methoxyanilino)-3-aminopyridine hydrochloride, m.p. 260° C.

Step C: Preparation of 3-(2-methoxyphenyl)-3H-1,2,3-triazolo[4,5-b]pyridine

The amino compound (4 g.) from Step B in 100 ml. of water was cooled in an ice bath and a solution of 1.1 g. of sodium nitrite in 25 ml. of water was added over 20 minutes, maintaining the temperature below 5° C. After an additional 20 minutes at room temperature the solids were collected (2.6 g., m.p. 154°–156° C.) and recrystallized from benzene-petroleum ether to give 2.3 g. of 3-(2-methoxyphenyl)-3H-1,2,3-triazolo[4,5-b]pyridine, m.p. 154°–156° C.

Employing the procedure substantially as described in Example 3, Steps A through C, but substituting for the 2-methoxyaniline used in Step A thereof an equimolar amount of 4-methylaniline, there is produced respectively:

Step A: 2-(4-methylanilino)-3-nitropyridine, m.p. 147–149;

Step B: 3-amino-2-(4-methylanilino)pyridine hydrochloride not characterized; and Step C: 3-(4-methylphenyl)-3H1,2,3-triazolo[4,5-b]pyridine, m.p. 114°–115° C.

EXAMPLE 4

3-(1,3-Dihydro-5-isobenzofuranyl)-3H-1,2,3-triazolo[4,5-b]pyridine

Step A: Preparation of 5-nitrophthalan

Phthalan (6 g., 0.05 mole) was dissolved in 75 ml. of concentrated sulfuric acid, cooled to 5° C., and with stirring a solution of 5.1 g. (0.05 mole) of potassium nitrate in 25 ml. of concentrated sulfuric acid was added dropwise over 40 minutes maintaining the temperature at <7° C. After an additional 30 minutes at ice-bath temperature and 30 minutes at room temperature, the solution was poured onto ice. The precipitate was collected and recrystallized from benzene-petroleum ether to give 5.5 g. of 5-nitrophthalan, m.p. 90°–92° C.

Step B: Preparation of 5-aminophthalan

The 5-nitrophthalan (19 g.) from Step A was hydrogenated in 200 ml. of methanol over 1 g. of 5% palladium on carbon for 30 minutes. The catalyst was removed by filtration, and the filtrate was evaporated to dryness to give 15.1 g. of product, m.p. 102–104. Recrystallization from benzene-petroleum ether gave 5-aminophthalan, m.p. 104–105.

Step C: Preparation of 2-(1,3-dihydro-5-isobenzofuranylamino)-3-nitropyridine

Employing the procedure substantially as described in Example 3, Step A, but substituting for the 2-methoxyaniline used therein an equimolar amount of 5-aminophthalan, there is produced 2-(1,3-dihydro-5-isobenzofuranylamino)-3-nitropyridine, m.p. 146°–147° C.

Step D: Preparation of 3-amino-2-(1,3-dihydro-5-isobenzofuranylamino)pyridine

The nitro compound (7.8 g.) from Step C was hydrogenated in 150 ml. of methanol over 0.5 g. of 5% palladium on carbon until close to the theoretical amount of hydrogen was absorbed. The catalyst was removed by filtration, and the filtrate was diluted with an excess of 2.5 N hydrochloric acid. Most of the methanol was evaporated in vacuo, and the residual solution was filtered.

Step E: Preparation of 3-(1,3-dihydro-5-isobenzofuranyl)-3H-1,2,3-triazolo[4,5-b]pyridine One-third of the acid solution from Step D was cooled in an ice-bath and with stirring a solution of 1 g. of sodium nitrite in 25 ml. of water was added over 20 minutes while maintaining the temperature below 5° C. After an additional 20 minutes at 5° C., the precipitate was collected (600 mg., m.p. 168°). The precipitate was dissolved in 25 ml. of warm benzene and filtered. The filtrate was treated with decolorizing carbon and the filtrate therefrom was concentrated to about 10 ml. and crystallization was induced by addition of petroleum-ether to give 350 mg. of 3-(1,3-dihydro-5-isobenzofuranyl)-3H-1,2,3-triazolo[4,5-b]pyridine, m.p. 174°–175° C.

Employing the procedure of Example 4, Steps C through E, but substituting for the 5-aminophthalan used in Step C thereof an equimolar amount of an amine of structure:

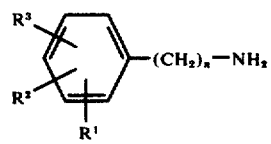

followed by reduction substantially as described in Step D thereof, followed by diazotization with sodium nitrite substantially as described in Step E, there are produced respectively the nitroaminopyridines, diaminopyridines, and 3H-1,2,3-triazolo[4,5-b]pyridines described in Table III in accordance with Equation I.

Table III

| Catalyst | R¹ | R² | R³ | R⁴ | n | m.p. (° C) Step A Product | m.p. (° C) Step C Product |
|---|---|---|---|---|---|---|---|
| Pd. | 2-OCH₃ | 4-OCH₃ | H | H | 0 | 139–140 | 163–164 |
| Pd. | 3-O—(CH₂)₂—O-4 | | H | H | 0 | 126–127 | 162–164 |
| Pd. | 3-OCH₃ | 4-OCH₃ | H | H | 0 | 97–98 | 137–138 |
| Pd. | 3-O—CH₂—O-4 | | H | H | 0 | 146–148 | 169–170 |
| Pd. | 3-OCH₃ | 4-OCH₃ | 5-OCH₃ | H | 0 | 139–140 | 138–140 |
| Pd. | 2-OCH₃ | 5-OCH₃ | H | H | 0 | 145–147 | 140–142 |
| Pd. | 3-CH₃ | 4-CH₃ | H | H | 0 | 134–136 | 110–111 |
| Pd. | 3-OCH₃ | 4-CH₃ | H | H | 0 | 101–102 | 132–133 |
| Pd. | 3-(CH₂)₃-4 | | H | H | 0 | 103–104 | 133–134 |

EXAMPLE 5

3-(4-Pyridyl)-3H-1,2,3-triazolo[4,5-b]pyridine

Step A: Preparation of 3-nitro-2-(4-pyridylamino)pyridine

A mixture of 4.0 g. 2-chloro-3-nitropyridine and 5.0 g. of 4-aminopyridine was heated in an oil bath until the internal temperature reaches 175° C. After cooling to room temperature, the solid product was extracted with 6 × 30 ml. of ethanol. The combined extracts were filtered and diluted with water to precipitate a solid (2 g.). The solid was collected, extracted with 3 × 150 ml. of ether and the combined extracts were concentrated to about 75 ml. The material that crystallized was collected to give 1 g. of 3-nitro-2-(4-pyridylamino)pyridine, m.p. 165°–167° C.

Step B: Preparation of 3-amino-2-(4-pyridylamino)pyridine

The nitro compound from Step A (1.0 g.) was hydrogenated in 60 ml. of methanol over 0.2 g. of 5% palladium on carbon catalyst. The catalyst was removed by filtration and the filtrate was evaporated to dryness.

Step C: Preparation of 3-(4-pyridyl)-3H-1,2,3-triazolo[4,5-b]pyridine

The residue from Step B (558 mg.) was dissolved in 10 ml. of water and 1 ml. of sulfuric acid. The solution was cooled in an ice-bath and treated dropwise with a solution of 0.21 g. of sodium nitrate in 2 ml. of water with stirring. After an additional 30 minutes in the ice-bath, the precipitate was collected (300 mg.).

The filtrate was neutralized with ammonium hydroxide and the precipitate was collected and recrystallized from 6 ml. of ethanol to give 3-(4-pyridyl)-3H-1,2,3-triazolo[4,5-b]pyridine, m.p. 196°–198° C.

The original precipitate of 300 mg. was extracted with 5 × 10 ml. boiling ethanol, keeping the 5 extracts separate. The crystalline product from extracts 2–5 were 3-(4-pyridyl)-3H-1,2,3-triazolo[4,5-b]pyridine sulfate, m.p. 221°–222° C. This was converted to the free base by solution in water and neutralization with ammonium hydroxide to give 3-(4-pyridyl)-3H-1,2,3-triazolo[4,5-b]pyridine, m.p. 196°–198° C.

EXAMPLE 6

3-(2-Methyl-6-pyridyl)-3H-1,2,3-triazolo[4,5-b]pyridine

Step A: Preparation of 2-(2-methyl-6-pyridylamino)-3-nitropyridine

A mixture of 4.0 g. of 2-chloro-3-nitropyridine and 3.3 g. 2-amino-6-methylpyridine was heated in an oil bath slowly to 175° C. The hot reaction mixture was decanted to a beaker causing crystallization. The solid mass was triturated with water and the solids (6 g.) were collected. Recrystallization from about 100 ml. of hot ethanol gave 2.5 g. of 2-(2-methyl-6-pyridylamino)-3-nitropyridine, m.p. 153°–154° C.

Step B: Preparation of 3-amino-2-(2-methyl-6-pyridylamino)-pyridine

The nitro compound (2.3 g.) from Step A was hydrogenated in 100 ml. of methanol over 0.4 g. of 5% palladium on carbon catalyst. The catalyst was removed by filtration, and the filtrate was concentrated to dryness.

Step C: Preparation of 3-(2-methyl-6-pyridyl)-3H-1,2,3-triazolo[4,5-b]pyridine A mixture of 1.0 g. of the crude amine from Step B, 20 ml. of water and 3 ml. of concentrated sulfuric acid was stirred, cooled to 0°–5° C. and treated dropwise with a solution of 0.345 g. of sodium nitrite in 2 ml. of water. After an additional hour at 0°–5° C. and storage at room temperature over the weekend, the precipitate was collected and recrystallized from 6 ml. of ethanol to give 3-(2-methyl-6-pyridyl)-3H-1,2,3-triazolo[4,5-b]pyridine, m.p. 144°–145° C.

Employing the procedure of Example 6, Steps A through C, but substituting for the 2-amino-6-methylpyridine used in Step A thereof, an equimolar amount of cyclohexylamine, there is produced in sequence:

2-(cyclohexylamino)-3-nitropyridine (oil); 3-amino-2-(cyclohexylamino)pyridine.HCl (not isolated); and 3-(cyclohexyl)-3H-1,2,3-triazolo[4,5-b]pyridine, m.p. 58°–59° C.

EXAMPLE 7

3-(2-Cyanophenyl)-3H-1,2,3-triazolo[4,5-b]pyridine

A mixture of 1 g. of 3-(2-bromophenyl)-3H-1,2,3-triazolo[4,5-b]pyridine and 1 g. of cuprous cyanide (CuCN) in 10 ml. of dry N-methylpyrrolidinone was purged with nitrogen and heated in an oil bath at 175° C. for 3 hours. After cooling to 50° C. a mixture of 40 ml. of ammonium hydroxide and 40 ml. of water was added. The precipitate was collected and washed with ammonium hydroxide-water (1:1) and water and air dried. The solid was extracted with 40 ml. of hot benzene. The benzene extract was cooled and diluted slightly with petroleum ether to give 600 mg. of 3-(2-cyanophenyl)-3H-1,2,3-triazolo[4,5-b]pyridine, m.p. 177°–179° C.

EXAMPLE 8

3-(2-Carbamoylphenyl)-3H-1,2,3-triazolo[4,5-b]pyridine

The cyano compound (from Example 7) (600 mg.) was dissolved in 8 ml. of concentrated sulfuric acid with ice cooling. After standing at room temperature for 7 hours it was poured onto ice. The cold solution was treated with an excess of ammonium hydroxide. The precipitate was collected, air dried and recrystallized from dimethylformamide and water to give 3-(2-carbamoylphenyl)-3H-1,2,3-triazolo[4,5-b]pyridine, m.p. >340° C.

EXAMPLE 9

3-(3-Carbamoylphenyl)-3H-1,2,3-triazolo[4,5-b]pyridine

Employing the procedure substantially as described in Example 8, but substituting for the 3-(2-cyanophenyl)-3H-1,2,3-triazolo[4,5-b]pyridine used therein an equimolar amount of 3-(3-cyanophenyl)-3H-1,2,3-triazolo-[4,5-b]pyridine, there is produced 3-(3-carbamoylphenyl)-3H-1,2,3-triazolo[4,5-b]pyridine, m.p. 237°–239° C.

EXAMPLE 10

3-(2-Hydroxyphenyl)-3H-1,2,3-triazolo[4,5-b]pyridine

A mixture of 1.2 g. of 3-(2-methoxyphenyl)-3H-1,2,3-triazolo[4,5-b]pyridine, 12.5 g. of aluminum chloride, and 175 ml. of dry benzene was refluxed 16 hours. The cooled mixture was stirred into ice-water containing 5 ml. of concentrated hydrochloric acid. The benzene layer was separated, washed with water and sodium bicarbonate solution, dried and evaporated to dryness. The residue was recrystallized from benzene to give 500 mg. of 3-(2-hydroxyphenyl)-3H-1,2,3-triazolo[4,5-b]pyridine, m.p. 165°–166° C.

EXAMPLE 11

3-(2,2-Dimethyl-1,3-benzodioxal-5-yl) 3H-1,2,3-triazolo[4,5-b]pyridine

Step A: Preparation of 2,2-dimethyl-1,3-dioxale

Catechol (20 g.) and 40 g. of phosphorus pentoxide were intimately mixed and 35 ml. of acetone was added portionwise. The mixture was cooled in ice and stirred until the reaction subsided and was then kept overnight at room temperature. Ice was added to decompose excess phosphorus pentoxide and the oily layer was extracted with 250 ml. of ether. The ether extract was washed with dilute sodium hydroxide solution to remove excess catechol. The ether was dried and evaporated to dryness leaving 22 g. of oily residue.

Step B: Preparation of 2,2-dimethyl-5-nitro-1,3-benzodioxole

The product from Step A (11 g.) was added over 45 minutes to 100 ml. of concentrated nitric acid while controlling the temperature to −5° C. After stirring 10 minutes at 0° C., it was poured into ice-water. The precipitate was collected, dissolved in 125 ml. of ether and filtered through aluminum oxide. Evaporation of the ether gave 13.5 g. of 2,2-dimethyl-5-nitro-1,3-benzodioxole, m.p. 89°–91° C.

Step C: Preparation of 5-amino-2,2-dimethyl-1,3-benzodioxole

The nitro compound from Step B (13.5 g.) was hydrogenated in 250 ml. of methanol over 0.5 g. of 5% palladium on carbon for 2 hours. The catalyst was removed, and the filtrate was evaporated to dryness. The residue was dissolved in benzene and again evaporated to dryness to give 11.6 g. of oily 5-amino-2,2-dimethyl-1,3-benzodioxole.

Step D: Preparation of 2-(2,2-dimethyl-1,3-benzodioxol-5-ylamino)-3-nitropyridine Prepared according to the process of Example 3, Step A, with:
2-chloro-3-nitropyridine (9.5 g.)
5-amino-2,2-dimethyl-1,3-benzodioxole (11.6 g.)
sodium acetate (5.7 g.)
acetic acid (200 ml.)
to give 11.5 g. of oil.

Step E: Preparation of 3-amino-2-(2,2-dimethyl-1,3-benzodioxol-5-ylamino)-pyridine hydrochloride Prepared according to the process of Example 3, Step B, with:
2-(2,2-dimethyl-1,3-benzodioxol-5-ylamino)-3-nitropyridine (11.5 g.)
methanol (175 ml.)
5% Pd/C (0.5 g.)
2.5 N hydrochloric acid (125 ml.)
to give an acid solution used directly in the next step.

Step F: Preparation of 3-(2,2-dimethyl-1,3-benzodioxol-5-yl) 3H-1,2,3-triazolo[4,5-b]pyridine Prepared according to the process of Example 3, Step C, with:
3-amino-2-(2,2-dimethyl-1,3-benzodioxol-5-ylamino)pyridine hydrochloride (42 ml.)
sodium nitrite (1.0 g.)
water (20 ml.)
to give 3-(2,2-dimethyl-1,3-benzodioxol-5-yl) 3H-1,2,3,-triazolo[4,5-b]pyridine, m.p. 122°–123° C.

EXAMPLE 12

3-(2,3-Dimethylbenzofuran-5-yl) 3H-1,2,3triazolo[4,5-b]pyridine

Step A: Preparation of 2,3-dimethyl-5-aminobenzofuran 2,3-Dimethyl-5-nitrobenzofuran (13.4 g.) was hydrogenated in 200 ml. of methanol over 0.6 g. of 5% palladium on carbon. The catalyst was removed by filtration and the filtrate was evaporated to dryness to give 2,3-dimethyl-5-aminobenzofuran, m.p. 77°–78° C.

Step B: Preparation of 2-(2,3-dimethylbenzofuran-5-ylamino-3-nitropyridine

Prepared according to the process of Example 2, Step A, with:
2chloro-3-nitropyridine (1.5 g.)
2,3-dimethyl-5-aminobenzofuran (3.0 g.)
reaction temperature (150° C.)
to give 1.7 g. of 2-(2,3-dimethylbenzofuran-5-ylamino-3-nitropyridine, m.p. 114°–116° C.

Step C: Preparation of 3-amino-2-(2,3-dimethylbenzofuran-5-ylamino)pyridine

Prepared according to the process of Example 2, Step B, using:
- 2-(2,3-dimethylbenzofuran-5-ylamino-3-nitropyridine (4.3 g.)
- methanol (300 ml.)
- 5% pd/C (0.5 g.)

to give 3-amino-2-(2,3-dimethylbenzofuran-5-ylamino)pyridine, m.p. 168°–170° C.

Step D: Preparation of 3-(2,3-dimethylbenzofuran-5-yl) 3H-1,2,3-triazolo[4,5-b]pyridine Prepared according to the process of Example 2, Step C, using:
- 3-amino-2-(2,3-dimethylbenzofuran-5-ylamino)pyridine (1.25 g.)
- 2.5 N hydrochloric acid (20 ml.)
- sodium nitrite (0.345 g.)
- water (1 ml.)

to give 3-(2,3-dimethylbenzofuran-5-yl) 3H-1,2,3-triazolo[4,5-b]pyridine, m.p. 152°–153° C.

EXAMPLE 13

3-(2-Methyl-4,5-methylenedioxyphenyl) 3H-1,2,3-triazolo-[4,5-b]pyridine

Step A: Preparation of 2-methyl-4,5-methylenedioxynitrobenzene

Piperonal (75 g.) was hydrogenated in 200 ml. of glacial acetic acid and 1 ml. of concentrated hydrochloric acid over 4 g. of 10% palladium on carbon. The catalyst was removed by filtration. The filtrate was cooled in acetone-dry ice and to it was added a mixture of 400 ml. of glacial acetic acid, 100 ml. of nitric acid ($d = 1.5$) and 60 ml. of 70% nitric acid. After 1 hour in the cold the mixture was allowed to warm to room temperature. It was poured onto ice and allowed to stand overnight. The precipitate was collected and recrystallized from 350 ml. of ethanol to give 57 g. of 2-methyl-4,5-methylenedioxynitrobenzene, m.p. 83°–84° C.

Step B: Preparation of 2-methyl-4,5-methylenedioxyaniline

The nitro compound (9.0 g.) from Step A was hydrogenated in 150 ml. of methanol over 500 mg. of 5% palladium on carbon for 30 minutes. The catalyst was removed by filtration and the filtrate was evaporated to dryness. Recrystallization of the residue gave 4.5 g. of 2-methyl-4,5-methylenedioxyaniline, m.p. 88°–89° C.

Step C: Preparation of 2-(2-methyl-4,5-methylenedioxyanilino)-3-nitropyridine Prepared according to the process of Example 2, Step A, from:
- 2-chloro-3-nitropyridine (500 mg.)
- 2-methyl-4,5-methylenedioxyaniline (1.0 g.)
- reaction temperature (150° C.)

to give 500 mg. of 2-(2-methyl-4,5-methylenedioxyanilino)-3-nitropyridine, m.p. 167°–168° C.

Step D: Preparation of 3-amino-2-(2-methyl-4,5-methylenedioxyanilino)pyridine Prepared according to the process of Example 2, Step B, including the conversion to the hydrochloride salt from:
- nitro compound from Step C (1.6 g.)
- methanol (75 ml.)
- 5% palladium on carbon (0.4 g.)

to give 750 mg. of 3-amino-2-(2-methyl-4,5-methylenedioxyanilino)pyridine, m.p. 180°–182° C.

Step E: Preparation of 3-(2-methyl-4,5-methylenedioxyphenyl) 3H-1,2,3-triazolo[4,5-b]pyridine Prepared according to the process of Example 2, Step C, from:
- amino compound from Step D (0.96 g.)
- 2.5 N hydrochloric acid (10 ml.)
- sodium nitrite (0.275 g.)
- water (1 ml.)

to give 800 mg. of 3-(2-methyl-4,5-methylenedioxyphenyl) 3H-1,2,3triazolo[4,5-b]pyridine, m.p. 147°–148° C.

EXAMPLE 14

1. Tablets — 10,000 scored tablets for oral use, each containing 250 mg. of active ingredient are prepared from the following ingredients:

|  | Gm. |
|---|---|
| 3-(2,5-difluorophenyl)-3H-1,2,3-triazolo[4,5-b]pyridine | 2500 |
| Starch, U.S.P. | 350 |
| Talc, U.S.P. | 250 |
| Calcium stearate | 35 |

The triazolopyridine compound is granulated with a 4% w./v. aqueous solution of methylcellulose U.S.P. (1500 cps.). To the dried granules is added a mixture of the remainder of the ingredients and the final mixture compressed into tablets of proper weight.

2. Capsules — 10,000 two-piece hard gelatin capsules for oral use, each containing 250 mg. of active ingredient are prepared from the following ingredients:

|  | Gm. |
|---|---|
| 3-(2-methyl-6-pyridyl)-3H-1,2,3-triazolo[4,5-b]pyridine | 2500 |
| Lactose, U.S.P. | 1000 |
| Starch, U.S.P. | 300 |
| Talc, U.S.P. | 65 |
| Calcium Stearate | 25 |

The triazolopyridine compound is mixed with the starch lactose mixture followed by the talc and calcium stearate. The final mixture is then encapsulated in the usual manner. Capsules containing 10, 25, 50, and 100 mg. of active ingredient are also prepared by substituting 100, 250, 500 and 1000 gm. for 2500 gm. in the above formulation.

3. Soft elastic capsules — One-piece soft elastic capsules for oral use, each containing 500 mg. of active material are prepared in the usual manner by first dispersing the active material in sufficient corn oil to render the material capsulatable.

4. Aqueous suspension — An aqueous suspension for oral use containing in each 5 ml., 250 mg. of active ingredient, is prepared from the following ingredients:

|  | Gm. |
| --- | --- |
| 3-(2,5-difluorophenyl)-3H-1,2,3-triazolo[4,5-b]pyridine | 500 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D. & C. orange dye | 7.5 |
| Deionized water, q.s. to 10,000 ml. | |

---

0.1 mg. disodium edetate
1.30 mg. of purified H₂O
300 mg. isopropanol
26 mg. hydroxypropylcellulose
q.s.a.d. 1 gm. propylene glycol
50 mg. 3-(2-methyl-6-pyridyl)-3H-1,2,3-triazolo[4,5-b]-pyridine

---

50 mg. wool alcohols B.P.
150 mg. Amerchol C
350 mg. white wax
q.s.a.d. 1 gm. isopropyl myristate
50 mg. 3-(2,5-difluorophenyl)-3H-1,2,3-triazolo[4,5-b]-pyridine

What is claimed is:

1. A compound of formula:

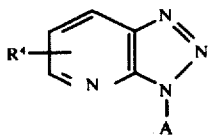

where A is
  1. pyridyl, either unsubstituted or substituted with lower alkyl,
  2. lower cycloalkyl,
  3.

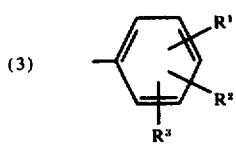

wherein R¹ and R² are the same or different and each is
  a. hydrogen,
  b. lower alkoxy,
  c. lower alkyl,
  d. halo,
  e. trifluoromethyl,
  f. amino, either unsubstituted or substituted with lower alkyl,
  g. phenoxy,
  h. hydroxy,
  i. lower alkanoyl, or R¹ and R² on adjacent carbon atoms taken together represent —(CH₂)₃—,
  R³ is
    a. hydrogen,
    b. lower alkoxy, or
    c. lower alkyl,
  R⁴ is
    1. hydrogen or
    2. lower alkyl.

2. The compound of claim 1 of formula:

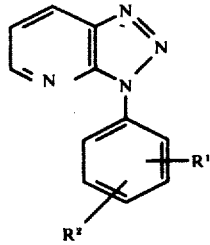

wherein R¹ and R² are the same or different and are hydrogen or fluoro.

3. The compound of claim 1 of formula:

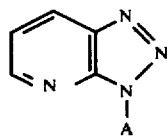

wherein A is pyridyl or lower alkylpyridyl.

4. A method of treating pain, inflammation or fever which comprises the administration to a patient in need of such treatment an effective amount of a compound of formula:

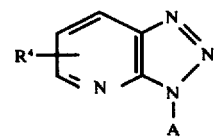

where A is
  1. pyridyl, either unsubstituted or substituted with lower alkyl,
  2. lower cycloalkyl,
  3.

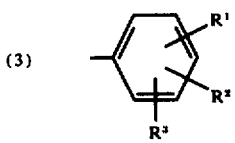

wherein R¹ and R² are the same or different and each is
  a. hydrogen,
  b. lower alkoxy,
  c. lower alkyl,
  d. halo,
  e. trifluoromethyl,
  f. amino, either unsubstituted or substituted with lower alkyl, g. phenoxy,
h. hydroxy,
i. lower alkanoyl,
or $R^1$ and $R^2$ on adjacent carbon atoms taken together represent —$(CH_2)_3$—,
 $R^3$ is
  a. hydrogen,
  b. lower alkoxy, or
  c. lower alkyl,
 $R^4$ is
  1. hydrogen or
  2. lower alkyl.

5. A pharmaceutical composition for treating pain, inflammation or fever comprising an inert carrier and an effective amount of a compound of formula:

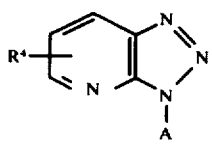

where A is
  1. pyridyl, either unsubstituted or substituted with lower alkyl,
  2. lower cycloalkyl,

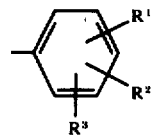

(3)

wherein $R^1$ and $R^2$ are the same or different and each is
  a. hydrogen,
  b. lower alkoxy,
  c. lower alkyl,
  d. halo,
  e. trifluoromethyl,
  f. amino, either unsubstituted or substituted with lower alkyl,
  g. phenoxy,
  h. hydroxy,
  i. lower alkanoyl,
or $R^1$ and $R^2$ on adjacent carbon atoms taken together represent —$(CH_2)_3$—,
 $R^3$ is
  a. hydrogen,
  b. lower alkoxy, or
  c. lower alkyl,
 $R^4$ is
  1. hydrogen or
  2. lower alkyl.

* * * * *